United States Patent
Hamada et al.

(10) Patent No.: US 7,894,047 B2
(45) Date of Patent: *Feb. 22, 2011

(54) BLOOD ANALYZER, SAMPLE ANALYZER, AND FLOW CYTOMETER

(75) Inventors: Yuichi Hamada, Kobe (JP); Kunio Ueno, Kakogawa (JP)

(73) Assignee: Sysmex Corporation, Hyogo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/509,111

(22) Filed: Jul. 24, 2009

(65) Prior Publication Data

US 2009/0310122 A1    Dec. 17, 2009

Related U.S. Application Data

(63) Continuation of application No. 11/398,548, filed on Apr. 6, 2006, now Pat. No. 7,580,120.

(30) Foreign Application Priority Data

Apr. 7, 2005    (JP) .............................. 2005-111411

(51) Int. Cl.
*G01N 33/48* (2006.01)
(52) U.S. Cl. ...................................... 356/39
(58) Field of Classification Search ................. 356/417, 356/39
See application file for complete search history.

(56) References Cited

U.S. PATENT DOCUMENTS

| 5,138,181 A | | 8/1992 | Lefevre et al. |
| 5,677,183 A | * | 10/1997 | Takarada et al. ............... 436/10 |
| 6,004,816 A | | 12/1999 | Mizukami et al. |
| 2002/0176069 A1 | | 11/2002 | Hansen et al. |
| 2006/0021437 A1 | * | 2/2006 | Kaduchak et al. ........... 73/570.5 |

FOREIGN PATENT DOCUMENTS

| WO | 88/07187 | 9/1988 |
| WO | 93/16384 | 8/1993 |
| WO | 94/29695 | 12/1994 |

OTHER PUBLICATIONS

Automated Hematology Analyzer XT-2000i/XT-1800i, Instructions for Use.
Automated Hematology Analyzer SF-3000 Operator's Manual.

* cited by examiner

*Primary Examiner*—Tarifur Chowdhury
*Assistant Examiner*—Abdullahi Nur
(74) *Attorney, Agent, or Firm*—Sughrue Mion, PLLC

(57) ABSTRACT

A sample analyzer is provided that is capable of eliciting sufficient performance of an avalanche photodiode, and performing high-precision analysis of the sample. The sample analyzer is provided with a WBC detection section that uses the avalanche photodiode as a photoreceptor element. The WBC detection section is provided with a flow cell, semiconductor light source, side collective lens, dichroic mirror, and avalanche photodiode. The side collective lens is a lens with a high NA (numeric aperture), and an aspheric lens with a small aberration. The sample analyzer prepares a scattergram using side fluorescent light signals and side scattered light signals to classify white blood cells into five categories.

9 Claims, 11 Drawing Sheets

BLOOD ANALYZER, SAMPLE ANALYZER, AND FLOW CYTOMETER

This is a Continuation application of U.S. application Ser. No. 11/398,548 filed Apr. 6, 2006, which claims priority from JP 2005-111411 filed Apr. 7, 2005, the contents of which are incorporated herein by reference.

FIELD OF THE INVENTION

The present invention relates to a blood analyzer for analyzing blood, a sample analyzer for analyzing samples containing particles, and a flow cytometer used in the sample analyzer.

BACKGROUND

Blood analyzers are known to count the numbers of red blood cells, white blood cells, and platelets. Such blood analyzers measure the red blood cells and platelets from a blood sample of diluted blood, and measure the white blood cells from samples of hemolyzed blood. Electrical resistance methods for detecting the electrical resistance of the sample, and flow cytometric methods for detecting the scattered light from a sample irradiated with light are used in these measurements. The electrical resistance signals employed in the measurements using the electrical resistance method and scattered light signals employed in the measurements using flow cytometry reflect the size of the blood cell, and red blood cells, white blood cells, and platelets can be counted using the signals.

Many such blood analyzers have the function of classifying white blood cells. White blood cell classification classifies white blood cells as lymphocytes, monocytes, neutrophils, eosinophils, and basophils. These types of white blood cells can not be classified simply by information on the size of the blood cell since there are very similar in size. In this case, white blood cells are classified by distributing blood in a plurality of aliquots, preparing a plurality of measurement samples by mixing different types of reagents in the respective aliquots, then measuring the plurality of measurement samples by various methods.

For example, the model SF-3000 manufactured by Sysmex corporation is configured to prepare a first measuring sample by admixing a reagent for four classifications of white blood cells in a first blood (aliquot), to irradiate the first measuring sample with light, to detect the low angle scattered light and high angle scattered light, and to classify white blood cells in four classifications of lymphocytes, monocytes, eosinophils, and a group comprised of neutrophils and basophils based on the low angle scattered light signals and high angle scattered light signals. On the other hand, SF-3000 is configured to prepare a second measuring sample by admixing a reagent for classifying basophils in a second blood (aliquot), to irradiate the second measuring sample with light, to detect the low angle scattered light and high angle scattered light, and to classify white blood cells in two classifications of basophils and other (lymphocytes, monocytes, neutrophils, and eosinophils) based on the low angle scattered light signals and high angle scattered light signals. And SF-3000 is capable of classifying white blood cells in five classifications from both classification results (refer to U.S. Pat. No. 5,677,183).

Similarly, dividing blood into two aliquots and preparing two types of measuring samples by mixing reagents with the respective aliquots, then measuring these aliquots and classifying the white blood cells in five categories is widely performed. For example, the models XE-2100i and XT-2000i manufactured by Sysmex Corporation are configured to prepare a first measuring sample by admixing a reagent for four classifications of white blood cells in a first blood, to irradiate the first measuring sample with light, to detect the side scattered light and fluorescent light, and to classify white blood cells in four classifications of lymphocytes, monocytes, eosinophils, and a group comprised of neutrophils and basophils based on the side scattered light signals and fluorescent light signals. On the other hand, XE-2100i and XT-2000i are configured to prepare a second measuring sample by admixing a reagent for basophil classification in a second blood, to irradiate the second measuring sample with light, to detect the forward scattered light and side scattered light, and to classify the white blood cells as basophils and other based on the forward scattered light signals and side scattered light signals.

Furthermore, the ADVIA manufactured by Bayer Corporation prepares a first measuring sample by admixing a reagent for four classifications of white blood cells in a first blood, irradiates the first measuring sample with light, detects the scattered light and absorbed light, then classifies the white blood cells in four classifications of lymphocytes, monocytes, eosinophils, and a group comprised of neutrophils and basophils based on the scattered light signals and absorbed light signals. The other hand, ADVIA prepares a second measuring sample by admixing a reagent for basophil classification in a second blood, irradiates the second measuring sample with light, detects the low angle scattered light and high angle scattered light, and classifies the white blood cells as basophils and other based on the low angle scattered light signals and high angle scattered light signals.

Still further, the Pentra manufactured by ABX Corporation prepares a first measuring sample by admixing a reagent for four classifications of white blood cells in a first blood, irradiates the first measuring sample with light, detects the absorbed light, detects the electrical resistance (impedance) in the first measuring sample, classifies the white blood cells in four classifications of lymphocytes, monocytes, eosinophils, and a group comprised of neutrophils and basophils based on the electrical resistance signals and absorbed light signals. The other hand, Pentra prepares a second measuring sample by admixing a basophil classification reagent in a second blood, detects the electrical resistance of the second measuring sample, and classifies as the basophils and other based on the electrical resistance signals.

Still further, apparatuses are provided that classify white blood cells from a single blood sample (aliquot). These apparatuses are configured to classify five types of white blood cells using three or more detection signals (for example, refer to U.S. Pat. No. 5,138,181). For example, the LH series of apparatuses manufactured by Beckman-Coulter Corporation prepare a single measuring sample by admixing a white blood cell classification reagent in a blood sample, irradiate the measuring sample with light, and detect the forward scattered light, as well as detect the direct current electrical resistance and high frequency electrical resistance in the measuring sample, and classify the white blood cells into five categories based on the three detection signals of the direct current electrical resistance signals, high frequency electrical resistance signals, and forward scattered light signals (refer to WO88/007187). Moreover, the Celldyn series of apparatuses manufactured by Abbott Laboratories prepares a single measuring sample by admixing a white blood cell classification reagent in a blood sample, irradiate the measuring sample with light, detect the scattered light at 0 degrees, scattered light at 10 degrees, 90 degree polarized scattered light, and 90 degree depolarized scattered light, and classifies white blood cells in five categories based on the 0 degree scattered light signals, 10 degree scattered light signals, 90 degree polarized scattered light signals, and 90 degree depolarized scattered light signals (refer to WO93/016384).

As described above, in conventional blood analyzers, a plurality of aliquots are required to classify white blood cells in five classifications, or three or more signals are required to classify white blood cells in five classifications by using a single aliquot. More blood is necessary when a plurality of aliquots are required than using a single aliquot, and a plurality of mixing chambers are required to prepare measuring samples from the respective aliquots. When three or more signals are needed, the structure of the apparatus becomes complex since many photoreceptor elements and electrical resistance detecting elements are required to detect the respective signals.

Furthermore, flow cytometers installed in such blood analyzers are provided with a flow cell through which the liquid of the sample flows, light source for irradiating the flow cell with light, and photoreceptor elements, such that the light from the light source is scattered by the particles (blood cells) in the flow cell, and fluorescent light is generated by particles stained with fluorescent dye that receive the irradiating light, the scattered light and fluorescent light is received by the photoreceptor elements, and the received light signals are analyzed in the process of analyzing the sample. Although photodiodes, photomultipliers and the like may be used as the photoreceptor elements, high sensitivity photomultipliers are generally used as the fluorescent photoreceptors due to the weakness of the fluorescent light compared to the scattered light. Further, a flow cytometer has been disclosed that uses avalanche photodiode (APD) as a fluorescent light photoreceptor as an alternative to the photomultiplier (refer to WO94/29695).

Since the avalanche photodiode has different sensitivity characteristics than other photoreceptors, such as typical photodiodes, photomultipliers and the like, adequate performance cannot be achieved by simply replacing other photoreceptors with the avalanche photodiode directly.

SUMMARY

The scope of the present invention is defined solely by the appended claims, and is not affected to any degree by the statements within this summary.

The first aspect of the present invention relates to a blood analyzer comprising: a preparation section for preparing a measurement sample by mixing at least a staining reagent for staining white blood cells with a blood sample; a detection section for detecting at least a first characteristic information and a second characteristic information representing characteristics of the measurement sample from the prepared measurement sample; and an analysis section for classifying the white blood cells contained in the measurement sample into five classifications based on the detected first characteristic information and second characteristic information; wherein the detection section comprises a light source for irradiating a measurement sample with light; and avalanche photodiode for receiving fluorescent light generated by irradiating a measurement sample with light from the light source and outputting a fluorescent light signal corresponding to the intensity of the received light, and the first characteristic information is the fluorescent light signal output from the avalanche photodiode.

The second aspect of the present invention relates to a sample analyzer comprising: a flow cell for forming a liquid flow of a sample containing particles; a light source for irradiating the flow cell with light; an avalanche photodiode for receiving light from a liquid flow in the flow cell irradiated with light by the light source; and an aspheric lens provided in the optical path connecting the flow cell and the avalanche photodiode.

The third aspect of the present invention relates to a flow cytometer comprising: a flow cell for forming a liquid flow of a sample containing particles; a light source for irradiating the flow cell with light; an avalanche photodiode for receiving light from a liquid flow in the flow cell irradiated with light by the light source; and an aspheric lens provided in the optical path connecting the flow cell and the avalanche photodiode.

DETAILED DESCRIPTION OF THE EMBODIMENT

The embodiment of the present invention is described hereinafter based on the drawings.

Figure 1:
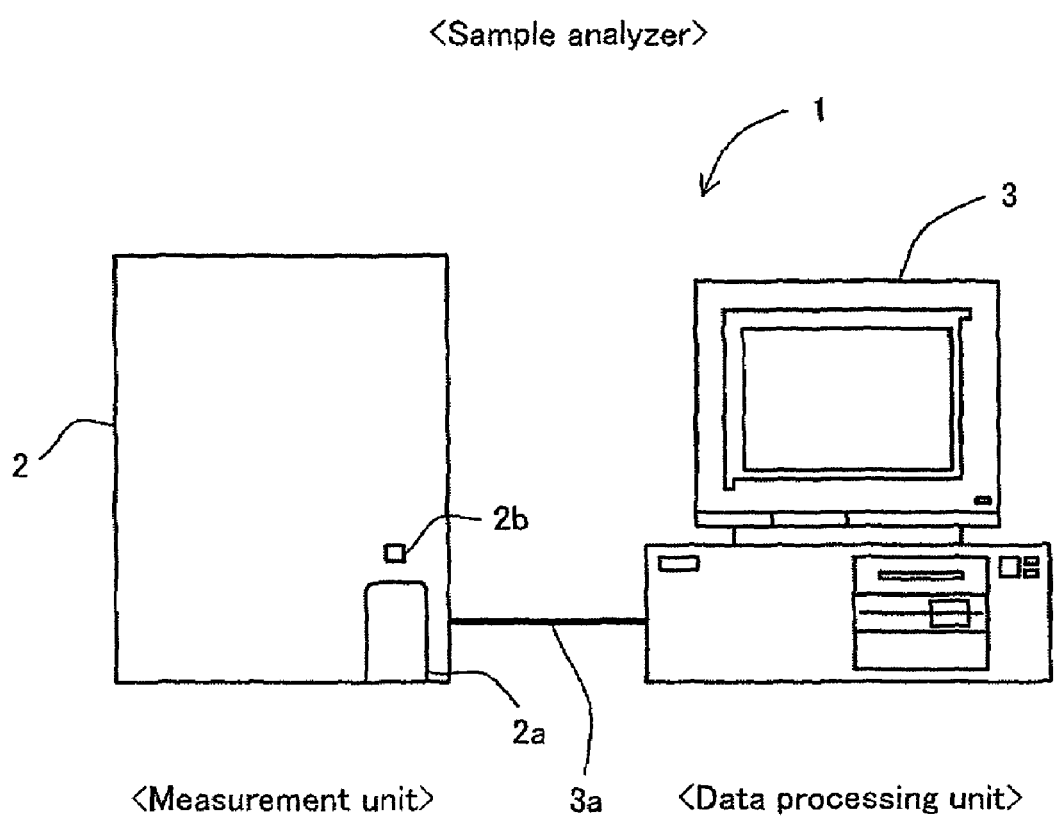
FIG. 1 is a front view briefly showing the structure of the sample analyzer of an embodiment.

FIG. 1 is a front view briefly showing the structure of the sample analyzer of an embodiment. As shown in FIG. 1, a sample analyzer 1 of the present embodiment is used in blood testings, comprises a measurement unit 2 and data processing unit 3. The measurement unit 2 performs predetermined measurements of components contained in blood specimens, and the measurement data are subjected to an analysis process when received by the data processing unit 3. The sample analyzer 1 is installed in medical facilities such as hospitals, or pathology laboratories and the like. The measurement unit 2 and data processing unit 3 are connected by a data transfer cable 3a so as to be capable of mutual data communications. the configuration is not limited to a direct connection between the measurement unit 1 and data processing unit 3 by the data transfer cable 3a, inasmuch as, for example, the measurement unit 2 and data processing unit 3 may also be connected through a dedicated line using a telephone line, or a communication network such as a LAN, Internet or the like.

Figure 2:
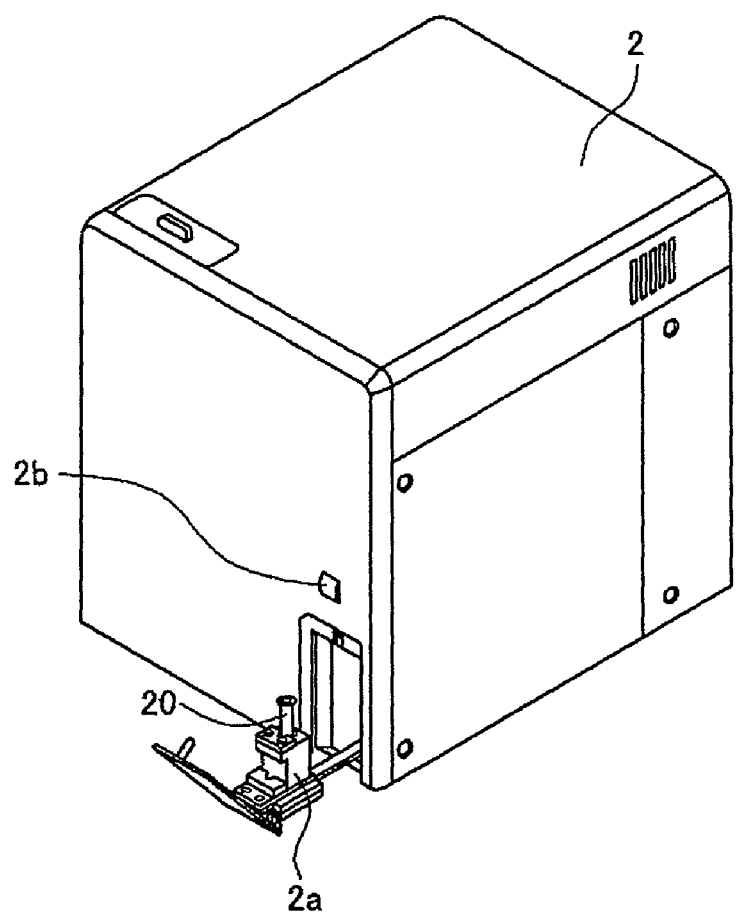
FIG. 2 is a perspective exterior view of the measurement unit provided in the sample analyzer of the embodiment.

FIG. 2 is a perspective view of the exterior of the measurement unit 2. As shown in FIG. 2, at the lower right of the front of the measurement unit 2, is provided with a blood collection tube placement unit 2a for placing a blood collection tube 20 that contains a blood sample. The blood collection tube placement unit 2a can receive a blood collection tube 20 placed therein by a user when a button switch 2b provided nearby is pressed by the user and the blood collection tube placement unit 2a moves in a forward direction. After the blood collection tube 20 has been placed, the user again presses the button switch 2b and the blood collection tube placement unit 2a withdraws and closes.

Figure 3:
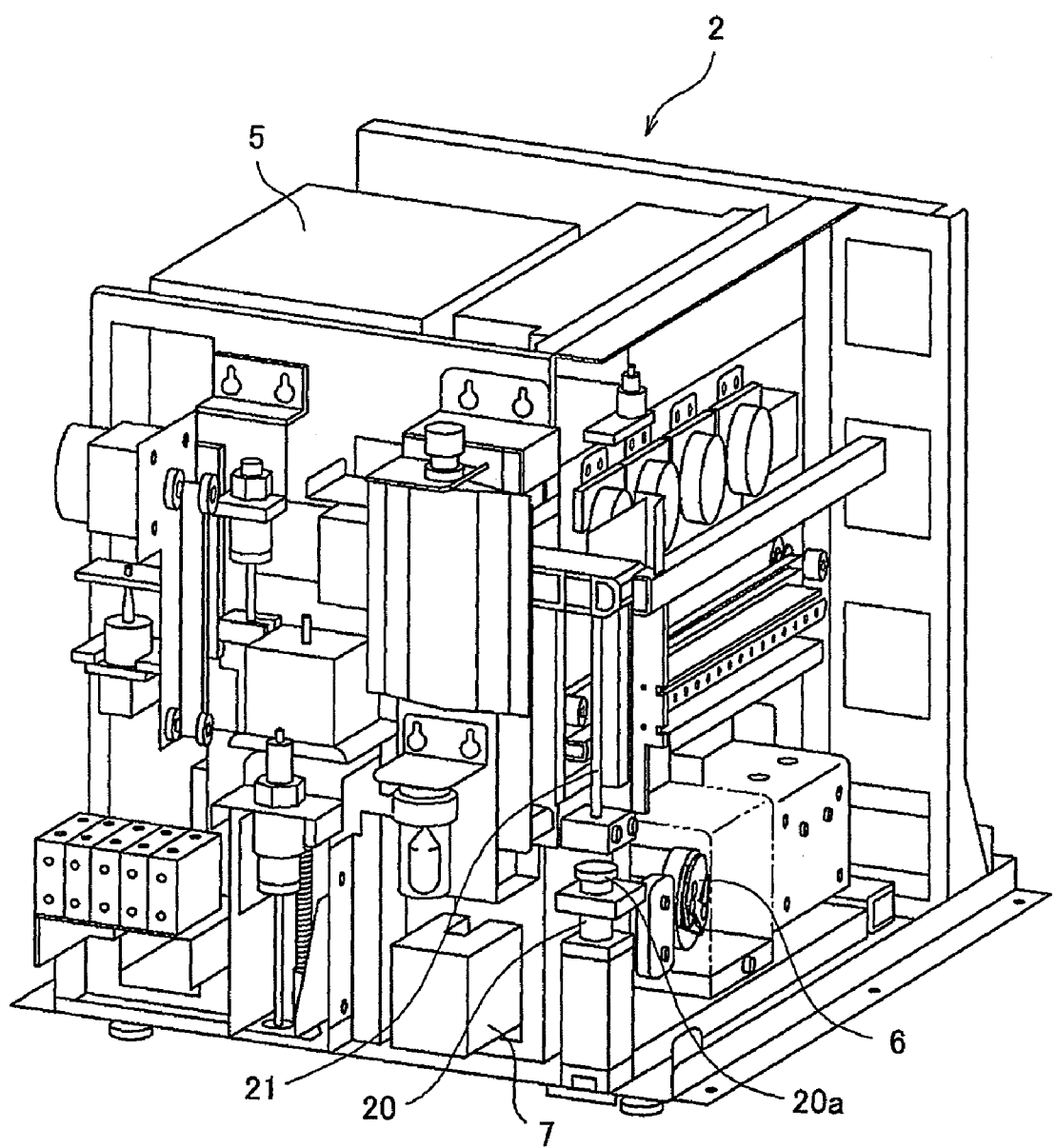
FIG. 3 is a perspective view showing the internal structure of the measurement unit provided in the sample analyzer of the embodiment.
Figure 4:
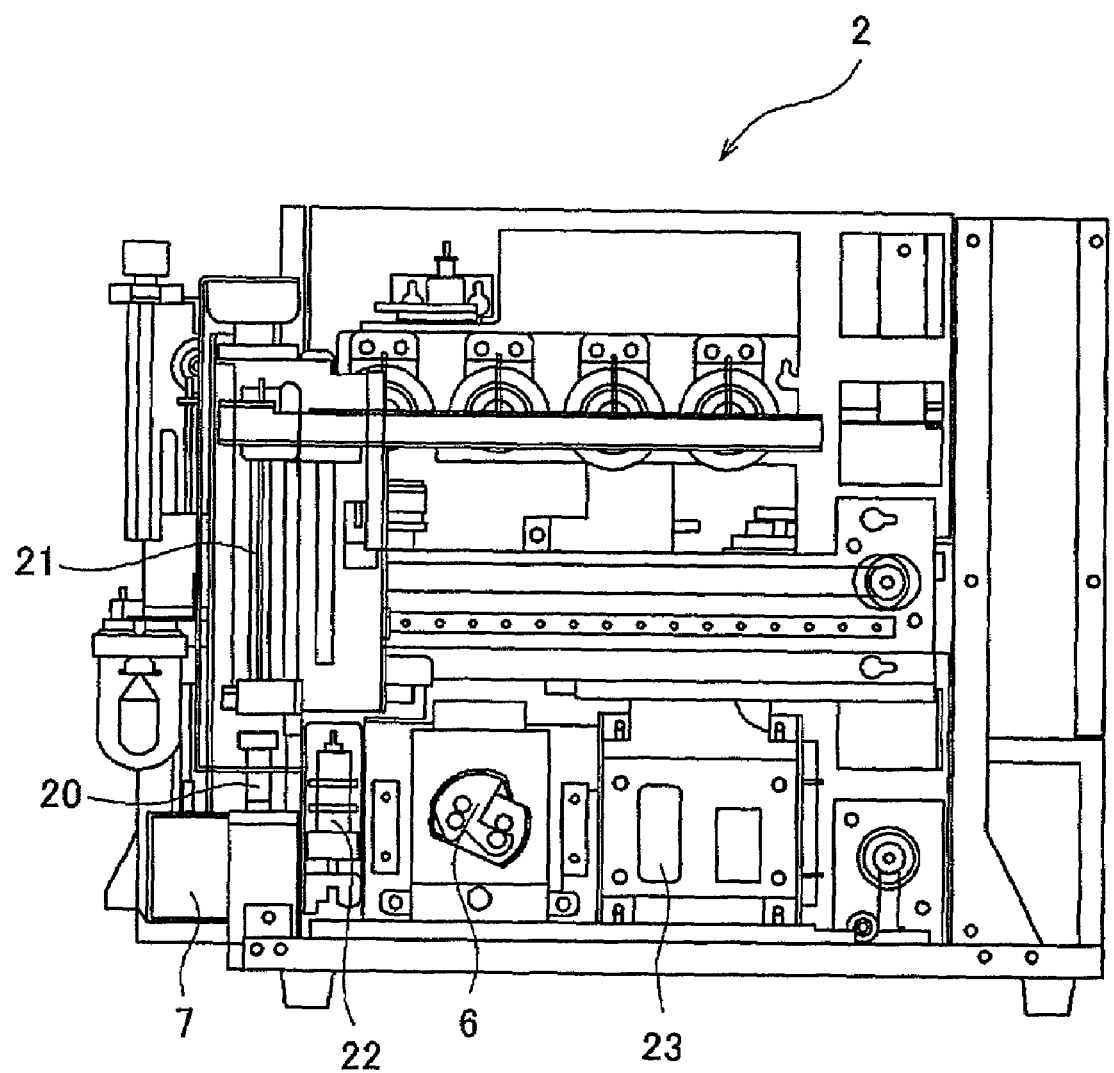
FIG. 4 is a side view showing the internal structure of the measurement unit provided in the sample analyzer of the embodiment.

FIG. 3 is a perspective view showing the interior structure of the measurement unit 2, and FIG. 4 is a side view of the same. The blood collection tube placement unit 2a holding the collection tube 20 is received within the measurement unit 2 as previously described, and the collection tube 20 is positioned at a predetermined suction position. A sample supply unit 4 including a pipette 21 for suctioning samples, chambers 22 and 23 for mixing and adjusting blood and reagent and the like is provided within the measurement unit 2. The pipette 21 is tube-like and extends vertically, and the tip is sharply tapered. The pipette 21 is linked to a syringe pump not shown in the drawing, and a predetermined amount of liquid can be suctioned or discharged by the operation of this syringe pump; the pipette 21 is also linked to a moving mechanism so as to be movable in vertical directions and forward and backward directions. The blood collection tube 20 is sealed by a rubber cap 20a, and the sharp tip of the pipette 21 pieces the cap 20a of the collection tube 20 placed at the suction position, and a predetermined amount of blood sample contained in the collection tube 20 can be suctioned by the pipette 21. As shown in FIG. 4, chambers 22 and 23 are provided behind the collection tube placement unit 2a; the pipette 21 is moved by the moving mechanism when the blood sample has been suctioned, and supplies the blood sample to the chambers 22 and 23 by discharging the blood sample into the chambers 22 and 23.

Figure 5:
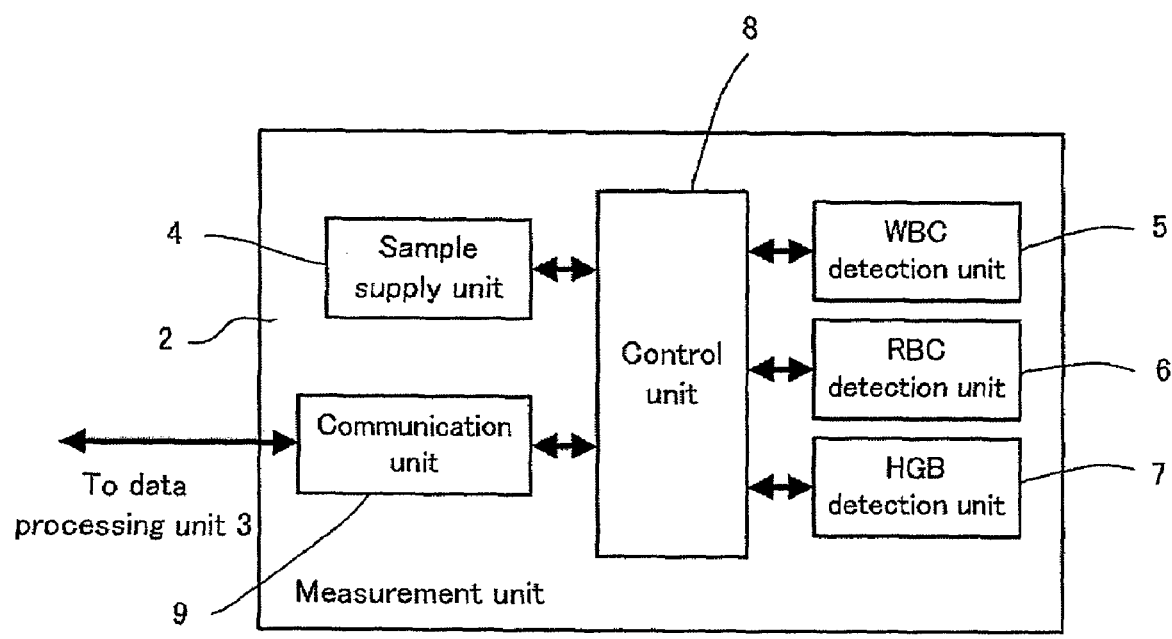
FIG. 5 is a block diagram showing the structure of the measurement unit provided in the sample analyzer of the embodiment.
Figure 6:
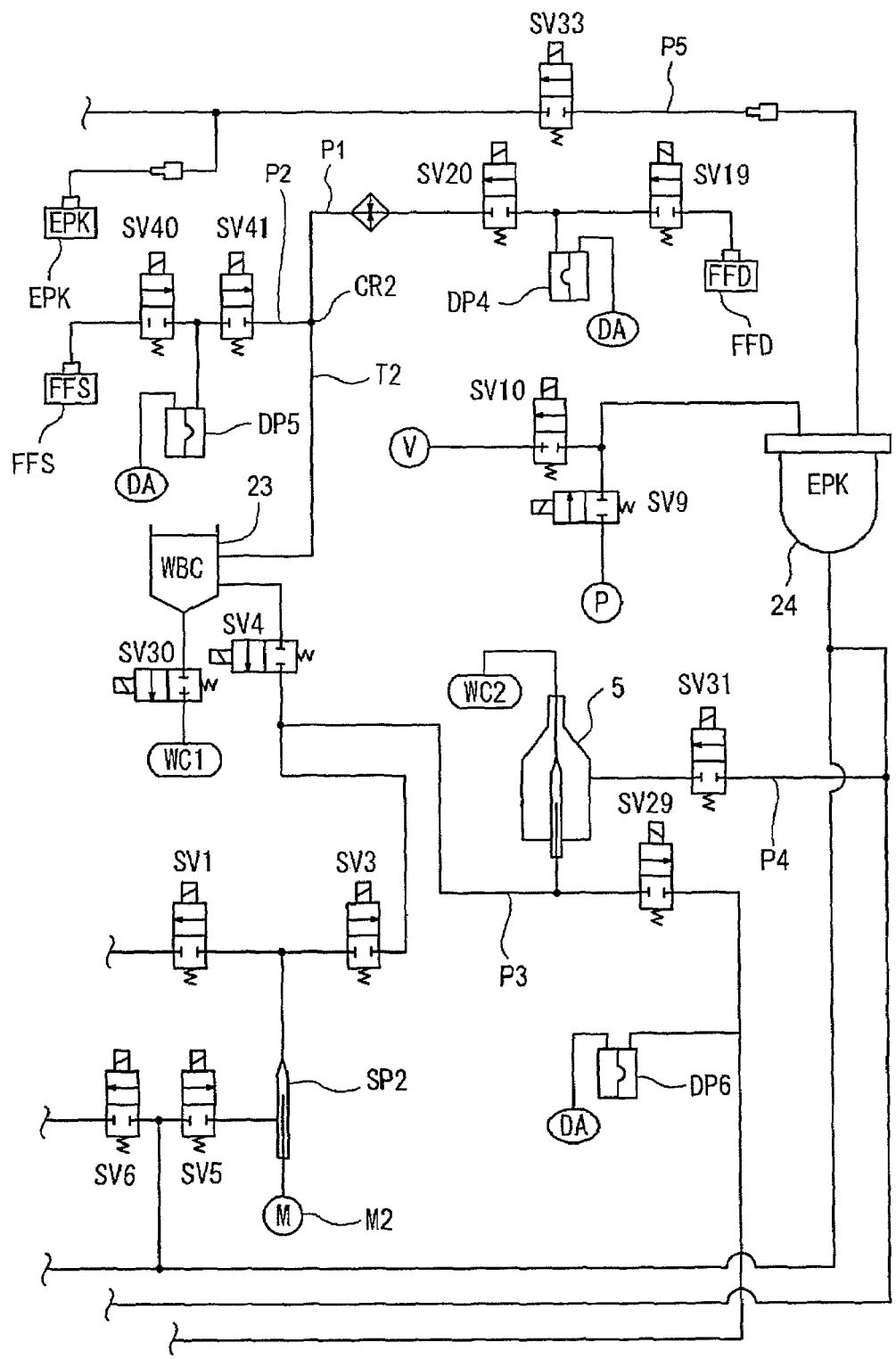
FIG. 6 is a fluid circuit diagram showing the structure of the sample supply section provided in the measurement unit.

FIG. 5 is a block diagram showing the structure of the measurement unit 2, and FIG. 6 is a flow circuit diagram showing the structure of the sample supply unit 4. As shown in FIG. 4, the measurement unit 2 is provided with a sample supply unit 4, WBC detection unit 5, RBC detection unit 6, HGB detection unit 7, control unit 8, and communication unit 9. The control unit 8 is configured by a CPU, ROM, RAM and the like, and performs operation control of each type of structural element of the measurement unit 2. The communication unit 9 is an interface, such as, for example, an RS-232C interface, USB interface, Ethernet (registered trademark), and is capable of sending and receiving data to/from the data processing unit 3.

As shown in FIG. 6, the sample supply unit 4 is a flow unit provided with a plurality of electromagnetic valves, diaphragm pumps and the like. Chamber 22 is used to adjust the sample supplied for the measurement of red blood cells and platelets, and the measurement of hemoglobin. The chamber 23 is used adjust the sample supplied for white blood cell measurement. FIG. 6 shows only the structure of the flow circuit on the periphery of the chamber 23 in order to simplify the drawing. The chamber 23 is connected to a reagent container FFD accommodating hemolytic agent and a reagent container FFS accommodating staining fluid through fluid flow paths P1 and P2, such as tubes or the like. Electromagnetic valves SV19 and SV20 are provided in the fluid flow path P1 connecting the chamber 23 and the reagent container FFD, and a diaphragm pump DP4 is provided between the electromagnetic valves SV19 and SV20. The diaphragm pump DP4 is connected to a positive pressure source and a negative pressure source, such that the diaphragm pump DP4 can be operated by positive pressure drive and negative pressure drive. Electromagnetic valves SV40 and SV41 are provided in the fluid flow path P2 connecting the chamber 23 and the reagent container FFS, and a diaphragm pump DP5 is provided between the electromagnetic valves SV40 and SV41.

The electromagnetic valves SV19, SV20, SV40, SV41, and diaphragm pumps DP4 and DP5 are operationally controlled as follows, and are capable of supplying hemolytic agent and staining fluid to the chamber 23. First, the electromagnetic valve SV19, which is disposed on the reagent container FFD side of the diaphragm pump DP4, is opened, and with the electromagnetic valve SV20, which is disposed on the chamber 23 side of the diaphragm pump DP4, in the closed state, a hemolytic agent is supplied in a fixed dosage from the reagent container FFD by negative pressure actuation of the diaphragm pump DP4. Thereafter, the electromagnetic valve SV19 is closed, the electromagnetic valve SV20 is opened, and the fixed quantity of hemolytic agent is supplied to the chamber 23 by positive pressure actuation of the diaphragm pump DP4. Similarly, the electromagnetic valve SV40, which is disposed on the reagent container FFS side of the diaphragm pump DP5, is opened, and with the electromagnetic valve SV41, which is disposed on the chamber 23 side of the diaphragm pump DP5, in the closed state, a staining fluid is supplied in a fixed dosage from the reagent container FFS by negative pressure actuation of the diaphragm pump DP5. Thereafter, the electromagnetic valve SV40 is closed, the electromagnetic valve SV41 is opened, and the fixed quantity of staining fluid is supplied to the chamber 23 by positive pressure actuation of the diaphragm pump DP5. Thus, the blood sample and reagents (hemolytic reagent and staining fluid) are mixed and the sample is adjusted for white blood cell measurement.

Furthermore, the chamber 23 is connected to the WBC detection unit flow cytometer through a fluid flow path P3 that includes tubes and an electromagnetic valve SV4. The fluid flow path P3 branches in its medial region, and electromagnetic valves SV1 and SV3 are connected in series at the branch point. A syringe pump SP2 is disposed medially to the electromagnetic valves SV1 and SV3. A stepping motor M2 is connected to the syringe pump SP2, such that the syringe pump SP2 is actuated by the operation of the stepping motor M2. Furthermore, the fluid flow path P3 connecting the chamber 23 and the WBC detection unit 5 also branches, and an electromagnetic valve SV29 and diaphragm pump DP6 are connected at the branch point. When white blood cells are measured by the WBC detection unit 5, the diaphragm pump DP6 is operated under negative pressure with the electromagnetic valves SV4 and SV29 in an open state, and the sample charges the fluid flow path P3 when the sample is suctioned from the chamber 23. When the sample charging is completed, the electromagnetic valves SV4 and SV29 are closed. Thereafter, the electromagnetic valve SV3 is opened, and the charged sample is supplied to the WBC detection unit 5 by operating the syringe pump SP2.

As shown in FIG. 6, the sample supply unit 4 is provided with a sheath fluid chamber 24, and the sheath fluid chamber 24 is connected to the WBC detection unit 5 through the fluid flow path P4. An electromagnetic valve SV31 is provided in the fluid flow path P4. The sheath fluid chamber 24 is a chamber for storing sheath fluid to be supplied to the WBC detection unit 5, and is connected to the sheath fluid container EPK that holds the sheath fluid through the fluid flow path P5 that includes tubes and an electromagnetic valve SV33. Before starting the measurement of white blood cells, the electromagnetic valve SV33 is opened and sheath fluid is supplied to the sheath fluid chamber 24, such that sheath fluid is stored in the sheath fluid chamber 24 beforehand. Then, when the measurement of white blood cells begins, the electromagnetic valve SV31 is opened, and sheath fluid stored in the sheath fluid chamber 24 is supplied to the WBC detection unit 5 simultaneously with the sample supplied to the WBC detection unit 5.

Figure 7:
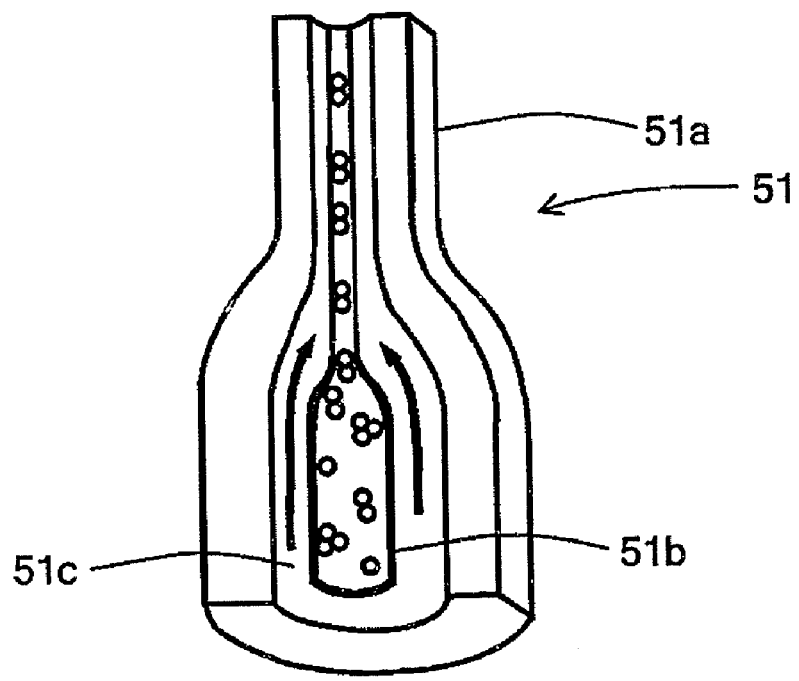
FIG. 7 is a perspective view schematically showing the structure of the flow cell provided in the measurement unit.

The WBC detection unit 5 is an optical type flow cytometer, and is capable of measuring white blood cells by a flow cytometry via a semiconductor laser. The WBC detection unit 5 is provided with a flow cell 51, which forms the fluid flow of the sample. FIG. 7 is a perspective view schematically showing the structure of the flow cell 51. The flow cell 51 is configured by a material such as transparent glass, glass, synthetic resin and the like, formed in a tube-like shape, and is a flow path through the interior of which the sheath fluid flows. The flow cell 51 is provided with an orifice 51a, the internal cavity of which has an aperture that is narrower than the other parts. The vicinity of the inlet of the orifice 51a of the flow cell 51 has a double-tube structure, and the internal side of this tube part becomes a sample nozzle 51b. The sample nozzle 51b is connected to the fluid flow path P3 of the sample supply unit 4, and sample is discharged through the sample nozzle 51b. Furthermore, the cavity on the outer side of the sample nozzle 51b is the flow path 51c through which the sheath fluid flows, and the flow path 51c is connected to the previously described fluid flow path P4. The sheath fluid supplied from the sheath fluid chamber 24 flows through the flow path 51c via the fluid flow path P4, and is introduced to the orifice 51a. The sheath fluid supplied to the flow cell 51 in this way flows so as to encapsulate the sample discharged from the sample nozzle 51b. Then, the sample flow is constricted by the orifice 51a, such that the particles of white blood cells and red blood cells contained in the sample are encapsulated in the sheath fluid and pass through the orifice 51a one by one.

Figure 8:
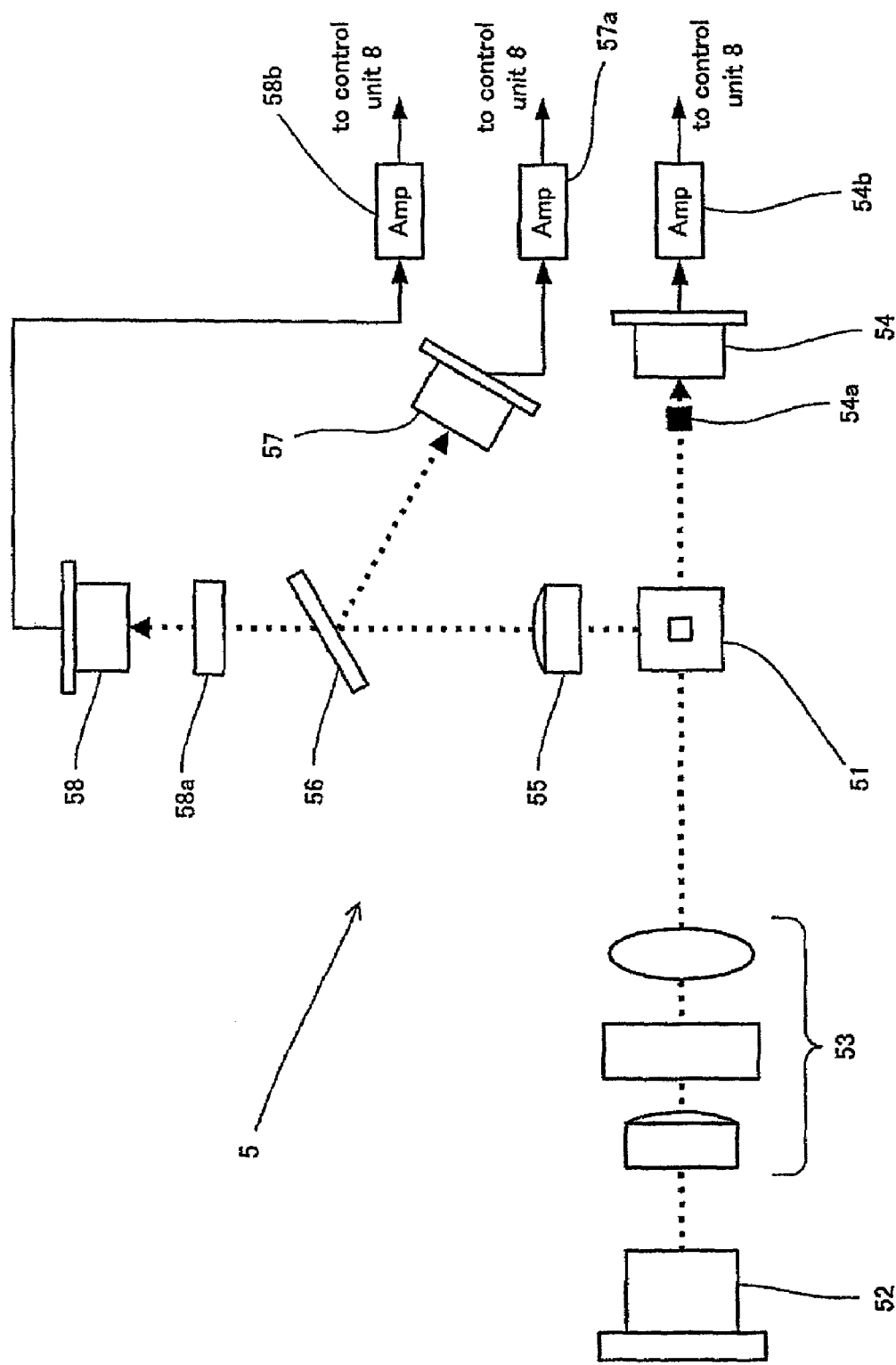
FIG. 8 is a brief plan view schematically showing the structure of the flow cytometer provided in the measurement unit.

FIG. 8 is a brief plan view that schematically shows the structure of the WBC detection unit 5. A semiconductor laser light source 52 is arranged in the WBC detection unit 5 so as to emit laser light toward the flow cell 51. An illumination lens system 53 including a plurality of lenses is arranged medially to the flow cell 51 and the semiconductor laser light source 52. Parallel beams emitted from the semiconductor laser light source 52 are collected at a beam spot by the illumination lens system 53. Furthermore, a beam stopper 54a is provided on the optical axis extending linearly from the semiconductor laser light source 52 so as to be opposite the illumination lens system 53 and with the flow cell 51 interposed therebetween. A photodiode 54 is arranged on the optical axis downstream of the beam stopper 54a.

When the sample flows through the flow cell 51, optical signals of scattered light and fluorescent light are generated by the laser light. Among these, the forward scattered light signals irradiate toward the photodiode 54. Among the light advancing along the optical axis extending linearly from the semiconductor laser 52, the direct light of the semiconductor laser 52 is blocked by the beam stopper 54a, and only the scattered light (hereinafter referred to as "forward scattered light") advancing along the optical axis direction enters the photodiode 54. The forward scattered light emitted from the flow cell 51 is subjected to photoelectric conversion by the photodiode 54, and the electrical signals (hereinafter referred to as "forward scattered light signals") generated by this conversion are amplified by an amplifier 54b, and output to the control unit 8. The forward scattered light signals reflect the size of the blood cells, and the size of the blood cells and the like can be obtained when the control unit 8 subjects the forward scattered light signals to signal processing.

Furthermore, a side collective lens 55 is arranged at the side of the flow cell 51, in a direction perpendicular to the optical axis extending linearly from the semiconductor laser light source 52 to the photodiode 54, and the lateral light (light emitted in a direction intersecting the optical axis) generated when the semiconductor laser irradiates the blood cells passing through the flow cell 51 is collected by the side collective lens 55. A dichroic mirror 56 is provided on the downstream side of the side collective lens 55, and the signal light transmitted from the side collective lens 55 is divided into a scattered light component and fluorescent light component by the dichroic mirror 56. A side scattered light photoreceptor photodiode 57 is provided at the side (the direction intersecting the direction of the optical axis connecting the side collective lens 55 and the dichroic mirror 56) of the dichroic mirror 56, and an optical filter 58a and avalanche photodiode 58 are provided on the optical axis on the downstream side of the dichroic mirror 56. Then, the side scattered light component separated by the dichroic mirror 56 is subjected to photoelectric conversion by the photodiode 57, and the electrical signals (hereinafter referred to as "side scattered light signals") generated by this conversion are amplified by an amplifier 57a and output to the control unit 8. The side scattered light signals reflect the internal information (size of the nucleus and the like) of the blood cells, and the size of the nucleus of the blood cell and the like can be obtained when the control unit 8 subjects the side scattered light signal to signal processing. Furthermore, the side fluorescent light component emitted from the dichroic mirror 56 is subjected to wavelength selection by the optical filter 58a, and subsequent photoelectric conversion by the avalanche photodiode 58, and the electrical signals (side fluorescent light signals) thus obtained are amplified by an amplifier 58b and output to the control unit 8. The side fluorescent light signals reflect information related to the degree of staining of the blood cells, and the stainability of the blood cells can be obtained by subjecting the side fluorescent light signals to signal processing.

The avalanche photodiode has the characteristic that the signal-to-noise S/N ratio of the output signals decrease as the acceptance surface increases. Furthermore, although the S/N ratio can be improved by increasing the intensity of the light emitted from the semiconductor laser 52, the effect decreases when the acceptance surface of the avalanche photodiode 58 is reduced, and such a solution is not desirable from the perspective of the energy consumption since the energy consumption increases as the level of the output light increases. Therefore, it is important to have the acceptance surface of the avalanche photodiode 58 as small as possible. When the acceptance surface of the avalanche photodiode 58 is reduced excessively, the acceptance surface may be smaller than the image of the particles imaged on the acceptance surface of the avalanche photodiode 58 by the side collective lens 55, in which case side fluorescent light signals that accurately reflect information related to the particles can not be obtained. Furthermore, although reducing the magnification power of the side collective lens 55 so as to reduce the image of the particle to be smaller than the acceptance surface can be considered, when the acceptance surface is excessively small, it becomes difficult to position the optical axis, thus requiring greater assembly precision and increasing costs.

Figure 9:
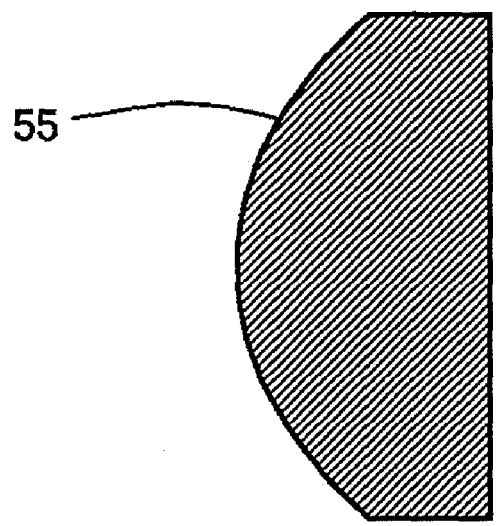
FIG. 9 is a side section view showing the shape of the side collective lens provided in the flow cytometer.

Moreover, although it is desirable that the acceptance surface of the avalanche photodiode 58 is small, when the acceptance surface is reduced, part of the particle image may be outside the acceptance surface depending on the degree of aberration of the side collective lens 55 manifesting the particle image that is formed on the acceptance surface. Therefore, the aberration of the side collective lens 55 must be reduced in conjunction with the smaller acceptance surface of the avalanche photodiode 58. Furthermore, the side collective lens 55 must have a high numeric aperture (NA) since the fluorescent light measured by the avalanche photodiode 58 is often weak. Accordingly, the side collective lens 55 is an aspheric lens. FIG. 9 is a side section view showing the shape of the side collective lens 55. The side collective lens 55 is a biconvex lens, in which the radius of curvature of the lens surface decreased from the center part toward the edge part. Although FIG. 9 shows the side collective lens 55 as a plano-convex lens, the apparently flat surface is actually slightly curved. Specifically, the shape of the lens surface of the side collective lens 55 is described by the equation below.

$$X = \frac{Co \cdot Y^2}{1 + \sqrt{1 - (K+1) \cdot Co^2 \cdot Y^2}} + \sum_{i=1}^{n} C_i \cdot Y^i$$

Where the following obtains.

X: position in the optical axis direction

Y: distance from the lens center in the direction in which the optical axis advances K: shape coefficient Co: coefficient representing the curvature of the base surface (spherical surface basis of the aspherical surface)

Ci: aspherical surface coefficient i: integers 1~n

The lens surface shape of the side collective lens 55 is a curved surface obtained when the curvature represented by the equation above is rotated about optical axis. The coefficients Co, K, and Ci match the lens magnification and focal length and the like, and are set at values that doe not generate aberration. Thus, the aberration readily generated at the edge of the lens can be suppressed. Furthermore, the NA of the side collective lens 55 is 0.60. In this way, the NA can be set high and the influence of lens aberration can be eliminated by having an aspheric lens of a shape that suppresses the generation of aberration. Therefore, the entire image of the particle is accurately formed on the acceptance surface of the avalanche photodiode 58 by the side collective lens 55, and the amount of light arriving at the acceptance surface of the avalanche photodiode 58 can be increased, with the result that weak fluorescent light can be detected by the avalanche photodiode 58.

Furthermore, the only lens provided at the side of the flow cell 51 is the single-piece aspheric surface side collective lens 55. although it is possible to suppress aberration by combining multiple spherical lenses, this solution would increase the cost, the amount of light would be reduced since the light would pass through a plurality of lenses, and the size of the flow cytometer would increase. Therefore, the cost can reduced, light loss can be suppressed, and the flow cytometer can be realized more compactly by the a structure in which the side scattered light and side fluorescent light is collected by a side collective lens 55 that is single-piece aspheric surface lens.

In this way, aberration is reduced by a side collective lens 55 that is an aspheric surface lens, and the acceptance surface of the avalanche photodiode 58 can be reduced. The size of the acceptance surface can be set in consideration of the size of the particle to be measured, the performance (NA, degree of aberration) of the side collective lens 55, output level of the semiconductor laser 52, and S/N ratio of the output signal of the avalanche photodiode 58. In the present embodiment, the white blood cells that are the measurement objects are usually approximately 7~20 ?m and present in peripheral blood, and since an aspheric lens having slight aberration is used, an avalanche photodiode 58 having a circular acceptance surface 1~2 mm in diameter may be used.

The RBC detection unit 6 can measure the number of red blood cells and platelets by a sheath flow DC detection method. The RBC detection unit 6 has a flow cell, and sample is supplied from the previously mentioned chamber 22 to the flow cell. When measuring red blood cells and platelets, a sample is prepared by mixing solution fluid with the blood in the chamber 22. The sample is supplied from the sample supply unit to the flow cell together with the sheath fluid, and a flow is formed in which the sample is encapsulated in the sheath fluid within the flow cell. Furthermore, an aperture with an electrode is provided in the flow path in the flow cell, and the direct current (DC) resistance in the aperture is detected when the blood cells in the sample pass thought the aperture one by one, and the electrical signal of the DC resistance is output to the control unit 8. since the DC resistance increases when the blood cell passes through the aperture, the electrical signal reflects information of the passage of the blood cell through the aperture, and the red blood cells and platelets can be counted by subjecting the electrical signals to signal processing.

The HGB detection unit 7 is capable of measuring the amount of hemoglobin by the SLS hemoglobin method. The HGB detection unit 7 is provided with a cell for accommodating dilute sample, sample is supplied from the chamber 22 to this cell. When measuring hemoglobin, a sample is prepared by mixing dilution liquid and hemolytic reagent in blood in the chamber 22. The hemolytic reagent has the characteristic of transforming hemoglobin in the blood to SLS hemoglobin. Furthermore, a light-emitting diode and photodiode are arranged in opposition with the cell interposed therebetween, and light emitted from the light-emitting diode is received by the photodiode. The light-emitting diode emits light of a wavelength that has high absorption by SLS hemoglobin, and the cell is formed of a plastic material of high transparency. Thus, in the photodiode, only the transmission light absorbed by the dilute sample is received among the light emitted by the light-emitting diode. The photodiode outputs electrical signals corresponding to the amount of received light (optical density) to the control unit 8, and the control unit 8 compares this optical density with the optical density of the dilution liquid alone which was measured beforehand, then calculates the hemoglobin value.

The control unit 8 receives the electrical signals from the WBC detection unit 5, RBC detection unit 6, HGB detection unit 7 as described above, and data representing the size of the blood cell, size of the nucleus of the blood cell, stainability of the blood cell, red blood cell count, platelet count, hemoglobin value and the like are transmitted from the control unit 8 to the data processing unit 3. The data processing unit 3 is configured by a computer provided with a CPU, ROM, RAM, hard disk, communication interface, input unit including a keyboard and mouse and the like, and a display device. The communication interface is, for example, an RS-232C interface, USB interface, Ethernet (registered trademark), and is capable of sending and receiving data to/from the measurement unit 2. Furthermore, an operating system, and application program for analyzing the measurement data received from the measurement unit 2 are installed on the hard disk of the data processing unit 3. In the data processing unit 3, measurement data are analyzed, white blood cell count (WBC), red blood cell count (RBC), hemoglobin amount (HGB), hematocrit value (HCT), mean red blood cell volume (MCV), mean red blood cell hemoglobin (MCH), mean red blood cell hemoglobin concentration (MCHC), platelet count (PLT), are calculated, and a scattergram is prepared using the side scattered light signals and side fluorescent light signals, and the white blood cells are classifies as neutrophils, lymphocytes, monocytes, eosinophils, and basophils when the CPU executes the application program.

The inventors performed experiments using the sample analyzer of the present embodiment. The experimental results are described below. In this experiment, white blood cells in blood samples were measured, and scattergrams prepared using the sample analyzer of the present embodiment, and a conventional sample analyzer (Sysmex model XE-2100) with a flow cytometer that receives fluorescent light.

Figure 10:
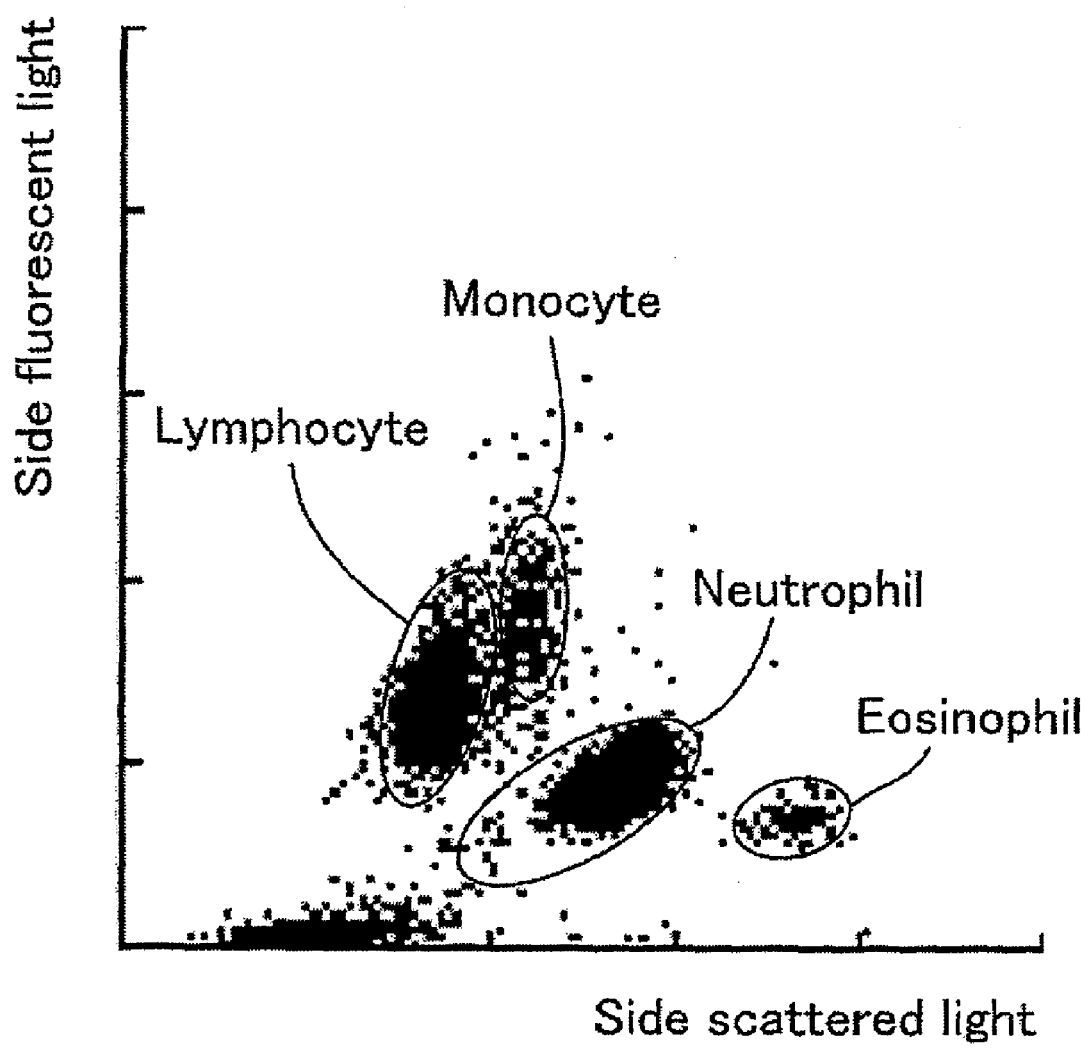
FIG. 10 is a scattergram showing the result of an experiment conducted using a conventional sample analyzer.
Figure 11:
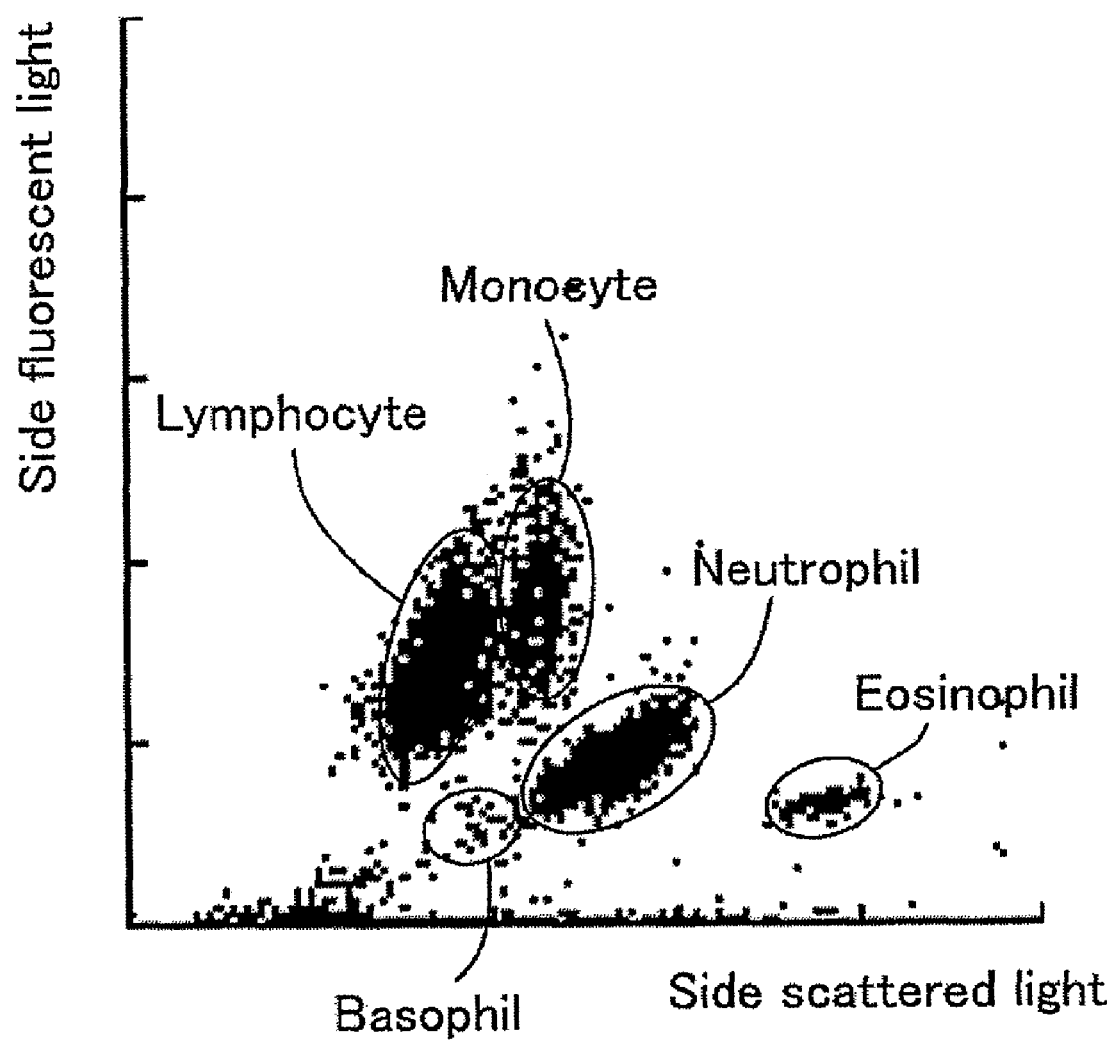
FIG. 11 is a scattergram showing the result of an experiment conducted using the sample analyzer of the embodiment.

FIG. 10 is a scattergram prepared using the conventional sample analyzer, and FIG. 11 is a scattergram prepared using the sample analyzer of the present embodiment. In FIGS. 10 and 11, the vertical axis shows the intensity of the side fluorescent light (level of received light), and the horizontal axis shows the intensity of the side scattered light (level of received light). In this experiment, measurement were performed using identical normal blood samples. Neutrophils, lymphocytes, monocytes, and eosinophils respectively formed definite clusters in the measurement results of the conventional sample analyzer as shown in FIG. 10. In the conventional sample analyzer, white blood cells were classified in four categories of neutrophils, lymphocytes, monocytes, and eosinophils, and basophils were not classified. Since the model XE-2100 used in this experiment is configured to perform four classifications in a measurement channel for classifying white blood cells, and detect only basophils in another separate measurement channel, the scattergram in this instance does not depict the region in which the basophils are present. Since the sample analyzer 1 of the present embodiment is configured to classify white blood cells as five classifications of neutrophils, lymphocytes, monocytes, eosinophils, and basophils all at the same time, the basophils are also depicted in the scattergram. In the measurement results of the sample analyzer of the present embodiment shown in FIG. 11, neutrophils, lymphocytes, monocytes, eosinophils, and basophils form definite clusters, and white blood cells are classified with high precision. Thus, analysis of white blood cells in blood samples can be performed with high precision using the sample analyzer of the present embodiment. Although omitted from the description, a similar experiment in classifying red blood cells as mature red blood cells and reticulocytes was performed and excellent results were obtained for both the conventional sample analyzer and the sample analyzer of the present embodiment.

Although the shape of the acceptance surface of the avalanche photodiode 58 is circular with a diameter of 1~2 mm in the present embodiment, the shape is not limited to this shape inasmuch as the diameter may be, for example, a circular shape of 0.1 mm to 1 mm, the shape may be square with an side length of 0.1~2 mm, or may be a rectangular shape having a surface area of the same degree.

Furthermore, although the side collective lens 55 is a biconvex aspheric lens in the present embodiment, the lens is not limited to this lens inasmuch as the side collective lens 55 may be a plano-convex aspheric lens insofar as the shape suppresses the generation of aberration.

Although the structure of the WBC detection unit 5, which uses the white blood cells in peripheral blood as the measurement object, is described in the resent embodiment, the detection unit is not limited to this structure inasmuch as blood cells other than white blood cells, such as megakaryocytes, reticulocytes, nucleated red blood cells, and the like, and macrophages that are nearly absent in peripheral blood although white blood cells may be included as measurement objects. In this case, the size of the acceptance surface of the avalanche photodiode 58 may be set so as to accurately detect the images of large cells such as megakaryocytes and macrophages.

Also in this case, a measurement sample may be prepared by mixing a blood sample and solution liquid and staining fluid without adding hemolytic reagent, and preparing a scattergram using the fluorescent light signals and side scattered light signals (for example, front scattered light signals), so as to classify reticulocytes, nucleated red blood cells, mature red blood cells, white blood cells and other blood cells.

Although the configuration of preparing a scattergram for five classifications of white blood cells using side fluorescent light signals and side scattered light signals has been described in the present embodiment, the configuration is not limited to this configuration inasmuch as the avalanche photodiode may be arranged forward of the flow cell to detect forward fluorescent light, so as to classify white blood cells in five classification by forward fluorescent light and side scattered light. Furthermore, a scattergram may be prepared using fluorescent light signals detected by the avalanche photodiode 58 and other signals, so as to classify white blood cells in five classifications. For example, forward scattered light signals may be used instead of side scattered light signals. Moreover, the position of the photoreceptor element may be changed so as to detect low angle scattered light and high angle scattered light, such that white blood cells can be classified in five classifications using fluorescent light signals, low angle scattered light signals, and high angle scattered light signals. A pair of electrode may be arranged to have the orifice 51a of the flow cell 51 interposed therebetween, so as to detect the DC resistance value or high frequency resistance value between the electrodes, whereupon the fluorescent light signals and DC resistance signals (characteristics are similar to forward scattered light signals) or high frequency resistance signals (characteristics are similar to side scattered light signals) can be used to classify white blood cells.

Although the configuration of a sample analyzer 1 for performing blood cell counts has been described in the present embodiment, the configuration is not limited to this configuration inasmuch as, for example, the sample analyzer may be configured for measuring particles in urine (urine solids) by means of a flow cytometer having an avalanche photodiode as a photoreceptor element, and a sample analyzer configured to measure cultured cells using a flow cytometer having an avalanche photodiode as a photoreceptor element.

Although the sample analyzer 1 is configured with the measurement unit 2 and data processing unit 3 provided separately in the present embodiment, the configuration is not limited to this configuration inasmuch as the sample analyzer may be an integrated unit possessing the functions of both the measuring unit 2 and the data processing unit 3.

The foregoing detailed description and accompanying drawings have been provided by way of explanation and illustration, and are not intended to limit the scope of the appended claims. Many variations in the presently preferred embodiments illustrated herein will be obvious to one of ordinary skill in the art, and remain within the scope of the appended claims and their equivalents.

What is claimed is:

1. A blood analyzer comprising:
a preparation section for preparing a measurement sample by mixing at least a staining reagent for staining white blood cells with a blood sample;
a detection section for detecting at least a first characteristic information and a second characteristic information representing characteristics of the measurement sample from the prepared measurement sample; and
an analysis section for classifying the white blood cells contained in the measurement sample into a plurality of classifications based on the detected first characteristic information and second characteristic information,
wherein the detection section comprises a light source for irradiating a measurement sample with light; and avalanche photodiode for receiving fluorescent light from the measurement sample irradiated with light and outputting a fluorescent light signal corresponding to the intensity of the received light, and
the first characteristic information is the fluorescent light signal output from the avalanche photodiode.

2. The blood analyzer according to claim 1, wherein the detection section comprises a light receiver for receiving scattered light from the measurement sample irradiated with light, and outputting a scattered light signal corresponding to the intensity of the received light, and
the second characteristic information is the scattered light signal output from the light reception section.

3. The blood analyzer according to claim 2, wherein the light receiver comprises a photodiode.

4. The blood analyzer according to claim 1, wherein the detection section comprises an electrical resistance detector for detecting the electrical resistance of the measurement sample, and
the second characteristic information is the electrical resistance signal output by the electrical resistance detector.

5. The blood analyzer according to claim 1, wherein the analysis section is configured so as to generate a scattergram based on the first characteristic information and the second characteristic information, and classify the white blood cells based on the generated scattergram.

6. The blood analyzer according to claim 1, wherein the detection section comprises:
a flow cell for forming a liquid flow of the measurement sample; and
an aspheric lens which light passes through from the flow cell, wherein the light source irradiates the measurement sample in the flow cell with light,
the avalanche photodiode receives the fluorescent light which has passed through the aspheric lens.

7. The blood analyzer according to claim 1, wherein the light source comprises a semi conductor laser.

8. Blood analyzing method comprising:
preparing a measurement sample by mixing at least a staining reagent for staining white blood cells with a blood sample;
irradiating the measurement sample with light;
receiving fluorescent light from the measurement sample irradiated with light by an avalanche photodiode, and scattered light from the measurement sample irradiated with light by a light reception section;
outputting a fluorescent light signal corresponding to the intensity of the received light from the avalanche photodiode, and a scattered light signal corresponding to the intensity of the received light from the light reception section; and
classifying the white blood cells contained in the measurement sample into a plurality of classifications based on the output fluorescent light signal and the output scattered light signal.

9. The blood analyzing method of claim 8, wherein the classifying comprising
generating a scattergram based on the fluorescent light signal and the scattered light signal; and
classifying the white blood cells based on the generated scattergram.

* * * * *